United States Patent
Montgomery et al.

(10) Patent No.: US 7,265,832 B2
(45) Date of Patent: Sep. 4, 2007

(54) OPTICAL FLOW METER FOR MEASURING GASES AND LIQUIDS IN PIPELINES

(75) Inventors: Derek Montgomery, New Westminster (CA); Daryl James, Burnaby (CA); David Yue Yan, Coquitlam (CA)

(73) Assignee: Photon Control Inc., Burnaby, British Columbia ( * ) Notice: Subject to any disclaimer, the term of this patent is extended or adjusted under 35 U.S.C. 154(b) by 0 days.

(21) Appl. No.: 10/570,323

(22) PCT Filed: Sep. 3, 2004

(86) PCT No.: PCT/CA2004/001593
§ 371 (c)(1),
(2), (4) Date: Oct. 3, 2006

(87) PCT Pub. No.: WO2005/022170
PCT Pub. Date: Mar. 10, 2005

(65) Prior Publication Data
US 2007/0064218 A1    Mar. 22, 2007

(30) Foreign Application Priority Data
Sep. 3, 2003    (CA) .................................... 2439242

(51) Int. Cl.
*G01P 3/36* (2006.01)
*G01N 21/00* (2006.01)
*G01F 1/708* (2006.01)

(52) U.S. Cl. ............... 356/338; 356/336; 356/337; 356/28; 250/574; 250/222.2; 73/861.05

(58) Field of Classification Search ........ 356/335–343, 356/28, 28.5; 250/573–575, 214 DC, 222.2; 73/861.05
See application file for complete search history.

(56) References Cited

U.S. PATENT DOCUMENTS 3,680,961 A * 8/1972 Rudd ......................... 356/335
4,201,467 A   5/1980 Hartmann et al.

(Continued)

FOREIGN PATENT DOCUMENTS

DE        4130526        3/1992

*Primary Examiner*—Sang H. Nguyen
(74) *Attorney, Agent, or Firm*—Oyen Wiggs Green & Mutal; Richard A. Johnson

(57) ABSTRACT

An optical system design for measuring the velocity of fluids flowing through pipes or other conduits is disclosed. The optical system is comprised of a means for delivering two beams through a window in the wall of the pipe, focused to two points aligned along an axis of the pipe and separated by a known distance, and means for detecting light that is scattered by particles carried in the fluid stream through a second window, that is disposed on the opposite side of the pipe. By measuring the time delay between detected signals, the velocity of the fluid can be determined. The delivered light beams are focused in a shallow cone of light and are blocked by an obstruction disposed behind the second window. The scattered light passes through an aperture behind the second window that surrounds the obscuration, and is focused on to a detector surface.

16 Claims, 11 Drawing Sheets

U.S. PATENT DOCUMENTS

| | | | |
|---|---|---|---|
| 4,251,733 A | | 2/1981 | Hirleman, Jr. |
| 4,707,130 A | * | 11/1987 | Hofmann et al. ............. 356/28 |
| 4,854,705 A | | 8/1989 | Bachalo |
| 4,919,536 A | * | 4/1990 | Komine ..................... 356/28.5 |
| 4,938,592 A | | 7/1990 | Poole et al. |
| 4,988,190 A | * | 1/1991 | Miles .......................... 356/28 |
| 5,133,602 A | * | 7/1992 | Batchelder et al. ......... 356/615 |
| 5,153,665 A | * | 10/1992 | Weinstein .................... 356/28 |
| 5,561,515 A | | 10/1996 | Hairston et al. |
| 5,905,568 A | * | 5/1999 | McDowell et al. ........... 356/28 |
| 5,999,256 A | * | 12/1999 | Jones et al. ................. 356/335 |
| 6,128,072 A | | 10/2000 | Kiel et al. |
| 6,429,926 B1 | | 8/2002 | Williamson et al. |
| 6,794,671 B2 | * | 9/2004 | Nicoli et al. ................ 250/574 |

* cited by examiner

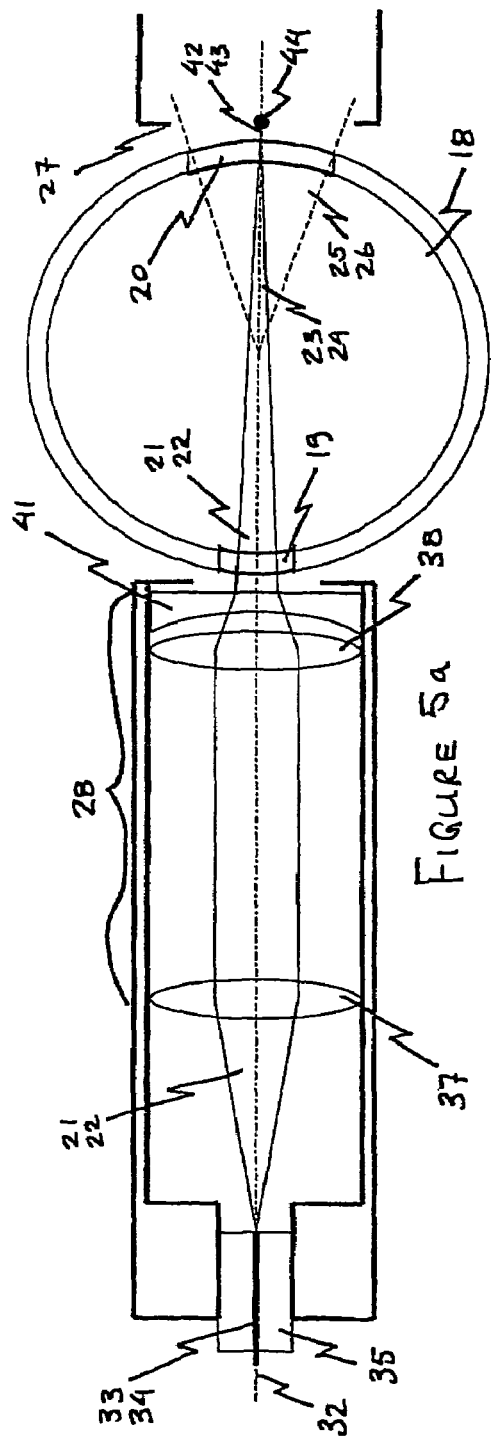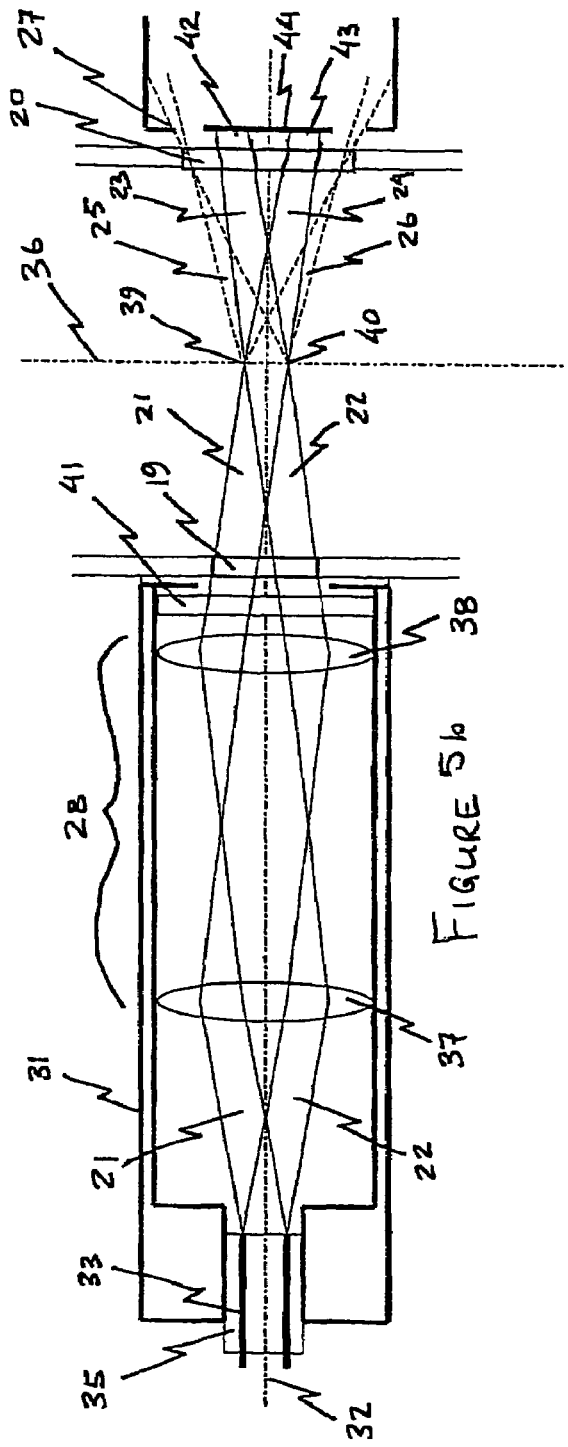

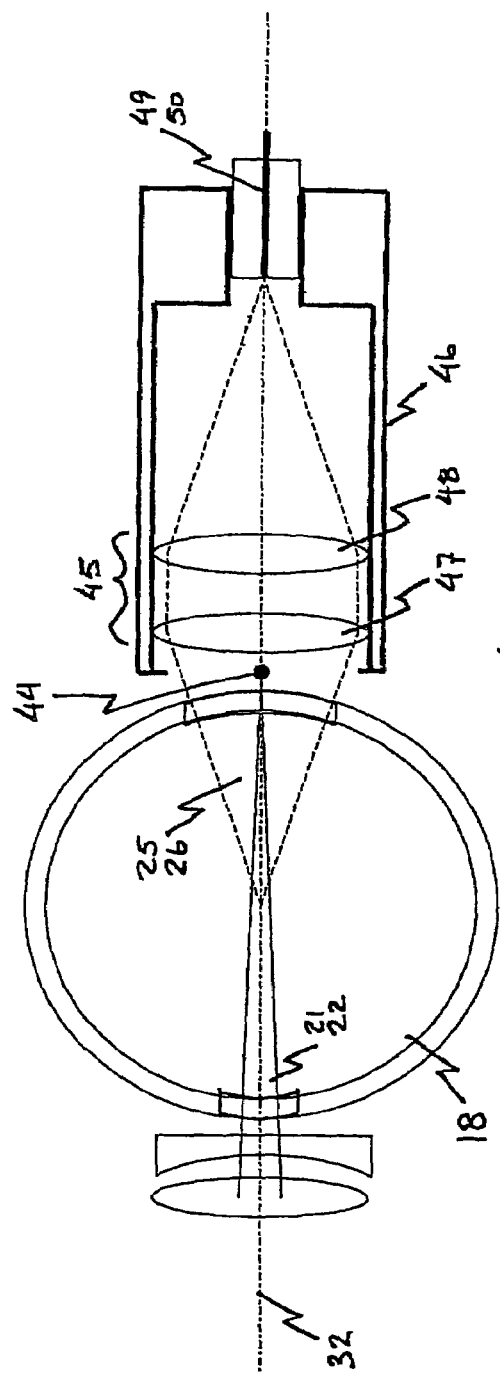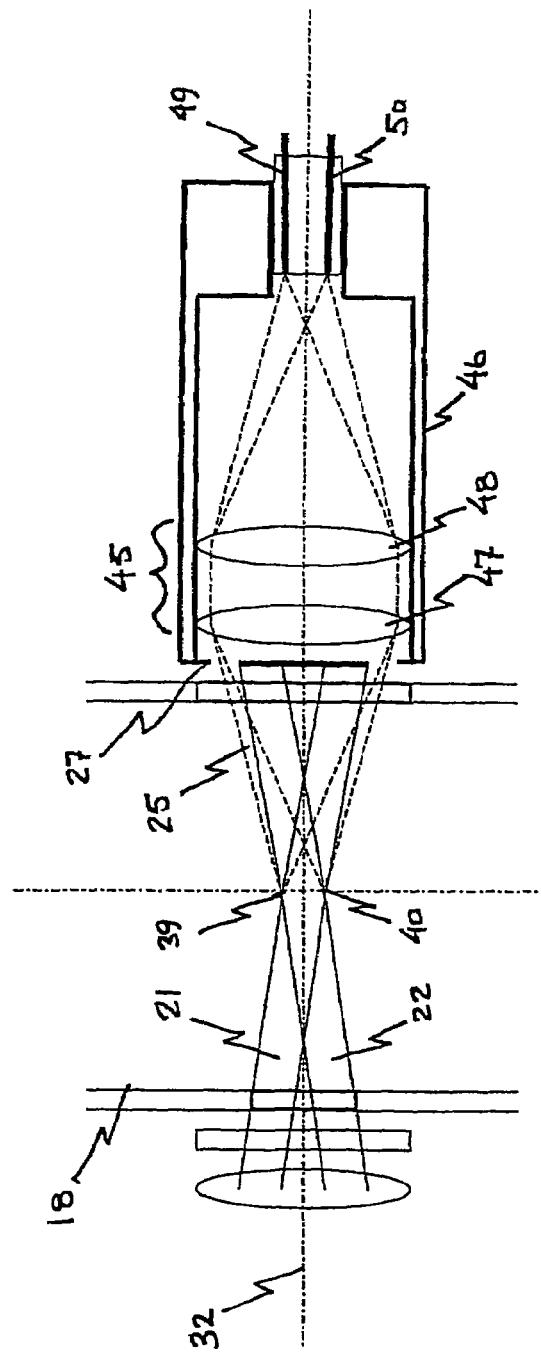

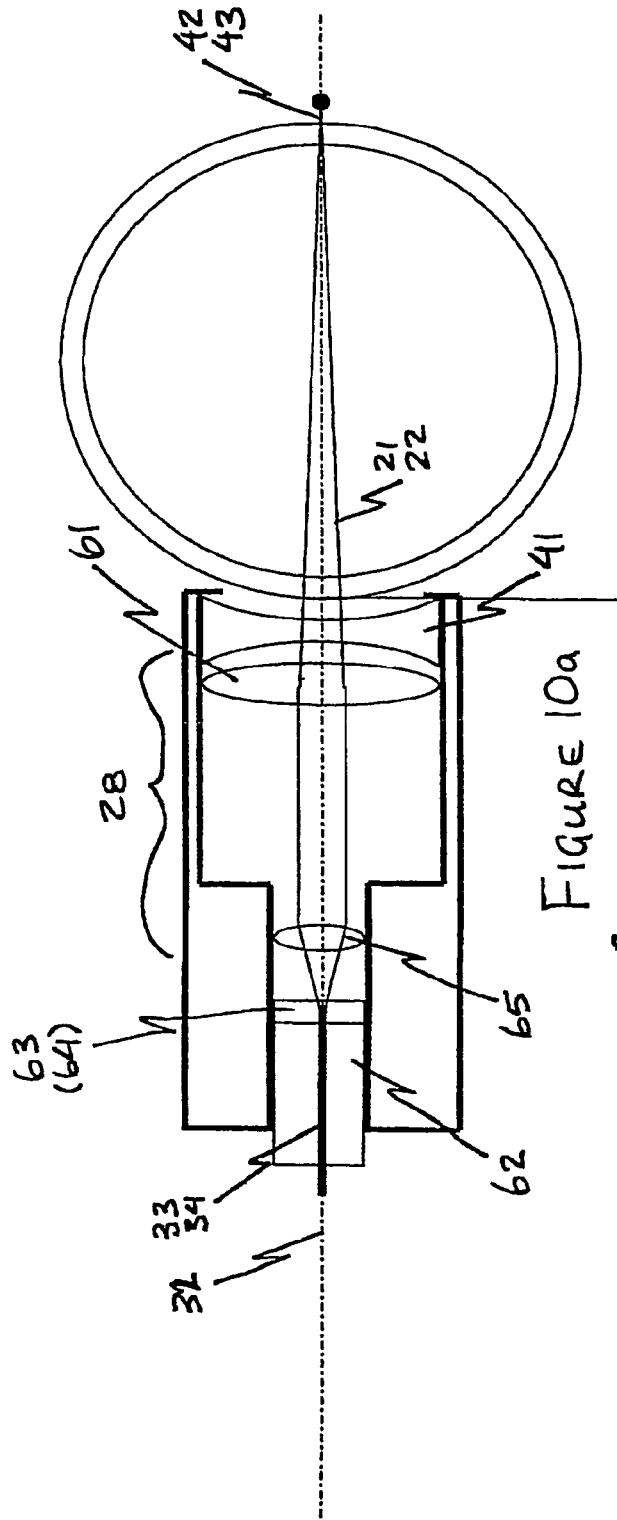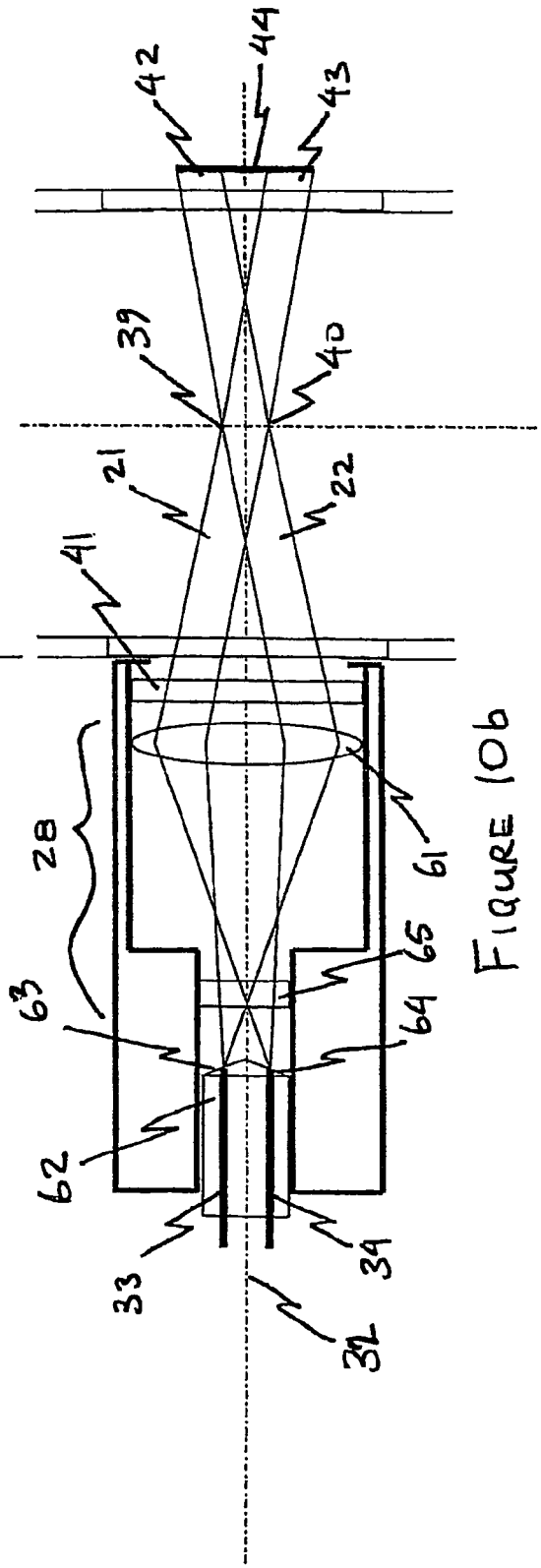
FIGURE 10a
FIGURE 10b

OPTICAL FLOW METER FOR MEASURING GASES AND LIQUIDS IN PIPELINES

BACKGROUND OF THE INVENTION

The present invention generally relates to metering devices for measuring the velocity of fluid flowing in a pipe, and is typically used to determine the flow volume rate in industrial applications, such as the transport of natural gas. More specifically, the invention relates to an optical system that focuses two light beams in the pipe through a transparent window in the pipe wall, and detecting the time of flight delay of light scattered by small particles carried by the fluid, as the particles pass from one focal spot to the other.

In pipeline operations and other industrial processes, flow meters are used to measure the flow rate of gases or fluids moving through the pipeline. There are many mechanical methods for determining the flow rate in pipes, including orifice plates, pitot tubes, Venturi meters, vortex meters, coriolis effect meters, variable area meters, and turbine meters, but generally they require that obstructive structures be inserted inside the pipe, which is undesirable in many applications because it disrupts the fluid flow and creates a pressure drop. Furthermore, many mechanical based sensors require that substantial gas pressures or flow rates be attained to produce a measurable effect. This is problematic for some applications where the reservoir pressure is very low, such as coal bed methane production, or when the fluid is vented to atmosphere or a large storage vessel.

Ultrasonic based meters are also known, which measure the Doppler shift of the acoustic velocity of ultrasound beams that are directed diagonally or along the pipe axis. Many ultrasound meters require pockets in the pipe walls to seat the ultrasound transducers, which is undesirable because contaminants tend to build up in the cavities. Long sections of pipe are required to accommodate the ultrasonic beam paths, which can be awkward and expensive, especially for large pipe diameters.

Other versions of ultrasonic flow meters launch the ultrasonic waves through the wall of the pipe, using clamp on transducers, but the accuracy performance suffers at low operating pressures and low flow rates.

Optical techniques for measuring the flow rate of fluids in pipes are also well known, and generally fall into two categories. Laser Doppler Anemometers use a single coherent laser that is split into two beams that are directed to intersect at the measurement point. The intersecting laser beams create an interference light pattern of alternating light and dark bands along the axis of the fluid flow. Particles passing through the measurement zone scatter the light, which creates a periodic varying optical signal, whose modulation frequency is proportional to the velocity of the particle. This technique is useful when measuring complex flows, where there are many large scattering particles, but because the light is distributed over many intensity maxima, the detection efficiency is low and small particles do not scatter enough light to be measured effectively.

The velocity of fluids can also be measured using a technique, generally referred to as the Laser-Two-Focus method. This system involves an optical delivery system that directs the light from one or two laser beams to form two focus spots in the pipe, separated by a known distance along the pipe axis. Particles in the fluid stream that pass through the two focus spots, scatter the light which is directed on to a photodetector by an optical collection system. The resulting signal consists of short impulses, and by measuring the time delay between adjacent pulses, the velocity of the particle can be determined. Because the intensity of the delivered light is concentrated in only two spots, the sensitivity of the Laser-Two-Focus method is superior to the Laser Doppler Anemometer system. This is important in certain fluids, such as natural gas, which contain only very small particles that are often less than 1 micron in diameter.

The amount of light scattered by a particle at a given angle depends on many variables, including the size, shape, surface quality, transparency/opacity, refractive index, and conductivity of the particles. The combination of these effects is very complex and generalized theories such as Mie and Rayleigh scattering fail to predict real world results accurately, so empirical studies are most often used to characterize specific systems. Mie theory is useful however in gaining a basic understanding of general trends in scattering behaviour. For instance it predicts that the amount of light scattered by very small particles (approaching the wavelength of the incident light or smaller), is subtended mostly within a very small, forward scatter angle. FIG. 1 shows that more than 90% of the light scattered by a spherical transparent droplet, with a diameter equal to 6 wavelengths of the incident light, occurs within a 10 degree forward angle cone.

The ability of a Laser Two Spot optical system to discriminate light scattered by a particle depends not only on the amount of light collected by the detection optics, but also by how much unscattered light is prevented from reaching the detector. For example, any light that is scattered at an angle less than the divergence cone of the incident light can not be effectively detected because the detector will be blinded by the unscattered light. The contrast or detectability of scattered light is fundamentally limited by the contrast ratio of detected scattered light to detected unscattered light.

Previous laser two spot optical flow meters, such as described by Kiel et al and Williamson et al, optimize the contrast of the detected light scatter signal, by shifting the optical axis of the collection optics away from the incident light axis, as shown in FIGS. 2a and 2b. This minimizes the signal bias caused by the unscattered light, but only a small amount of the scattered light is coupled into the collection aperture. In some cases, such as natural gas, where the size of naturally occurring scattering particles is very small, this can be a limiting factor and the signal to noise ratio will suffer due to weak detected scattered light levels.

Laser two spot anemometers are also known to characterize the flow of relatively large particles (greater than 10 wavelengths of the incident light) such as particulate dusts or aerosols. Hairston et al teaches a system for measuring the size and velocity of aerosols ejected by a nozzle, using the laser two spot method, with the collection aperture colinear with the incident beam axis. The unscattered light is blocked by a central obscuration located on the opposite side of the measurement zone, and light scattered at larger angles that pass into the collection aperture are focused on to a photodetector. Because the particles are relatively large in this application, the detected light amplitude is not so much a concern, so a large central obscuration can be used without sacrificing sensitivity.

The optical systems described by Kiel, Williamson, Hairston et al., all feature telecentric or parallel optical systems, that generate delivery light beams that are directed perpendicular to the flow direction. This is important in some applications, particularly when the fluid is a gas under high pressure. Most low pressure gases have a refractive index vary near unity, but at high reservoir pressures, greater gas density causes a significant increase in the refractive index, which would change the optical refraction angle of any light passing into the medium. This can cause a parallax type shift in the spacing between the focus spots, if the optical axis is not perpendicular to the flow axis, resulting in a measurement error.

In some flow measurement environments, such as natural gas wells, a significant amount of water, liquid hydrocarbons, particulates, and other contaminants may deposit on the optical windows and degrade the efficiency of the transmitted light over time. This problem has not been effectively addressed in the prior art for applications where the optical metering apparatus is intended to be left in place for long periods of time. Optical windows are used in many other pipeline applications, particularly sight glasses, and there are a number of remedies that have been developed to allow for the windows to be cleaned from time to time. It is desirable however, to develop an optical system that both resists fouling and is tolerant of variations in the optical transmission efficiency.

Also, for many industrial applications, information on size and shape of the particles flowing in the pipe is highly desirable to characterize and monitor the quality of the fluid in the process. This data verifies, for example, the quality of filtering means used at a natural gas processing plant, condition of the pumps and corrosion level of the pipes. Specialized laser devices for measuring particle size are known, but their use has been largely limited to controlled laboratory environments and they are not considered suitable for in-field applications due to their sensitivity to vibration and misalignments.

SUMMARY OF THE INVENTION

Therefore, it is an object of the invention to provide a device for determining the flow velocity of a fluid in a pipe, by measuring the time of flight delay of light scattered by small particles carried by the fluid, from two focused beams of light aligned along the pipe axis with a known separation distance between them.

It is an object of the invention to provide a fluid flow meter device that can be inserted in a thin gap in a pipe, and has smooth walls matched to the inner diameter of the mating pipe sections, so as not to disrupt the flow of the fluid within the pipe.

It is also an object of the invention to maximize the sensitivity of the optical system detection. More specifically, it is an object of the invention to maximize the efficiency of detected scattered radiation and minimize the detection of unscattered incident light.

It is also an object of the invention to provide an optical system that can compensate for fouling of optical windows in the pipe walls, caused by a build up of contaminants transported in the fluid stream, by monitoring the transparency of the windows and adjusting the gain of the optical detectors.

It is also an object of the invention to provide an optical system that is insensitive to refractive index changes in the transported gases that are compressed at high operating pressures.

Yet another object is to provide an optical system that can also characterize the size and shape of the scattering particles carried in the fluid stream, by measuring the amount of light scattered at large angles relative to the amount of light collected over small forward angles.

To achieve these and other objects, there is provided an apparatus for measuring the velocity of small particles carried by a fluid flowing through a pipe. The velocity measurement is most commonly used to determine the flow rate of the fluid inside the pipe. The apparatus includes at least one light source and a first optical lens system to generate two beams of light and direct the beams through a first window in the pipe wall to form a pair of focus spots in the volume of the pipe, at the same location in the pipe cross-section but separated along an axis parallel to the flow direction. Small particles carried in the fluid stream which travel along a trajectory coincident with the two focal points, scatter the light in succession and the time delay between scatter occurrences is inversely proportional to the particle velocity.

A second window is also provided in the pipe wall approximately opposing the first window, whereby means are provided to collect a portion of the scattered light that passes through the second window aperture, and to direct the scattered light by means of a second optical lens system, on to a light detector means. To improve the signal detection integrity, two light detector means may be deployed in the focal plane of the second optical system, each aligned to accept light scattered by a respective focus spot.

Means are also provided to block the unscattered light using an opaque obscuration positioned to intercept the beams at or behind the second window to prevent the unscattered light from reaching the detector. The obscuration is sized to block most or all of the unscattered light, but is smaller than the aperture of the second window to maximize the contrast of the detected scattered light.

The first optical system, first window, the second window, opaque obscuration and second optical system are approximately centered on a common optical axis that is approximately perpendicular to the pipe flow direction. The two beams of light are directed along the same common optical axis but the focus spots are separated laterally at the focal planes by approximately equal distance from the central axis. The apparatus is further characterized as having a pipe axis which is parallel to the flow direction, and a transverse axis which is perpendicular to both the optical axis and the pipe axis. Means are also provided to reduce the beam convergence of the light entering the pipe, in the transverse axis, to widen the focal spots and present a larger scattering cross-section to particles traveling in the fluid stream.

Further means are provided to convert the detected light into electrical signals that are approximately proportional to the incident light intensity. As a scattered particle passes through each focal point a pulse of light is scattered and received by the respective detector, and generates an electrical pulse. Means are provided to electronically determine the time delay between electrical pulses, and the velocity of the particles can be calculated if the distance between the focal spots is known. Further means are provided to determine the flow rate, which is approximately proportional to the particle velocity.

BRIEF DESCRIPTION OF THE DRAWINGS

For a further appreciation of the above and other features and advantages of the invention, reference is made to the following detailed description and drawings, in which:

FIGS. 5a and 5b are cross-sectional views, respectively along and perpendicular to the pipe axis, showing the delivery optical system of the preferred embodiment, exaggerated in size relative to the pipe cross-section, for greater clarity;

FIGS. 6a and 6b are cross-sectional views, respectively along and perpendicular to the pipe axis, showing the collection optical system of the preferred embodiment, exaggerated in size relative to the pipe cross-section, for greater clarity;

FIGS. 10a and 10b are cross-section views, respectively along and perpendicular to the pipe axis, showing an alternate embodiment of the present invention, comprised of a modified ferrule with facets polished at angle relative to the optical system axis, and a single coupling lens provided to focus the delivery beams and maintain the chief rays parallel with the optical axis through the pipe section;

DETAILED DESCRIPTION OF THE PREFERRED EMBODIMENTS

Figure 1:
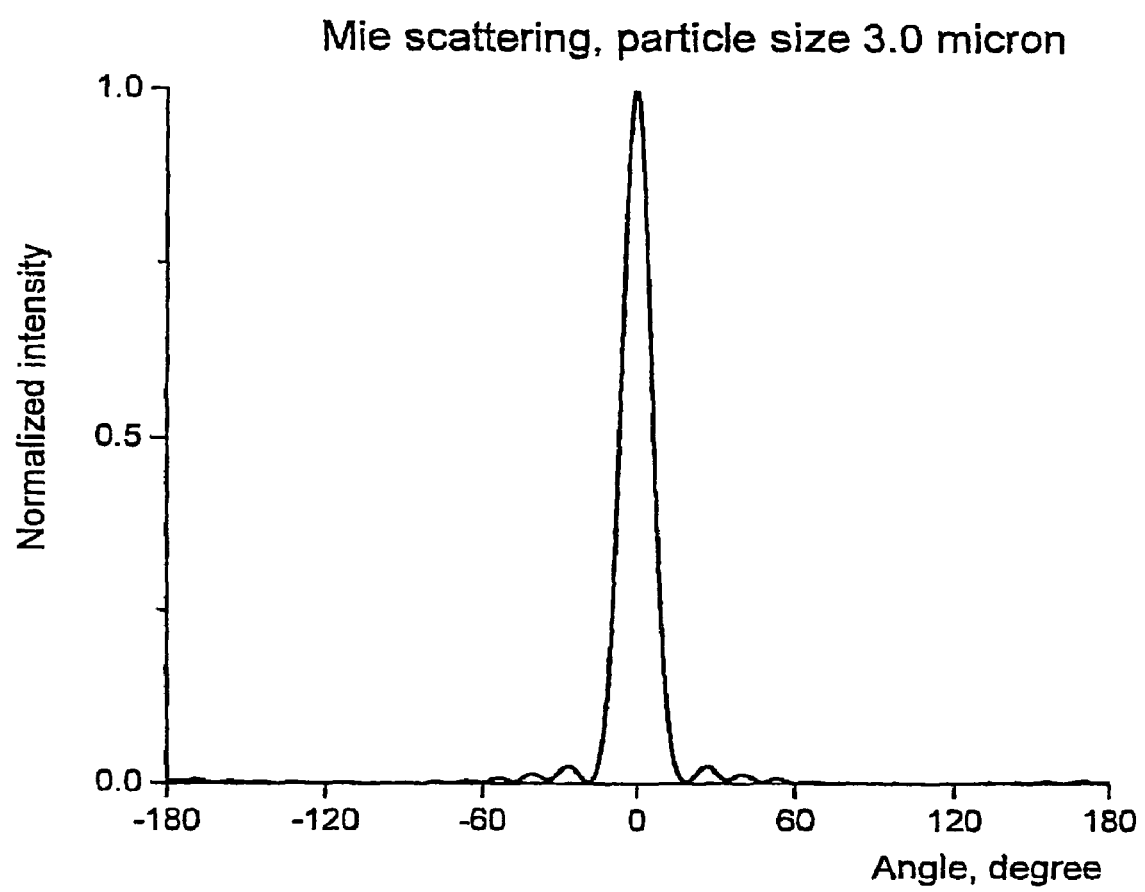
FIG. 1 is a diagram of the scattering light efficiency as a function of forward scatter angle of a 3 micron oil droplet, using a light wavelength of 650 nm.
Figure 2A:
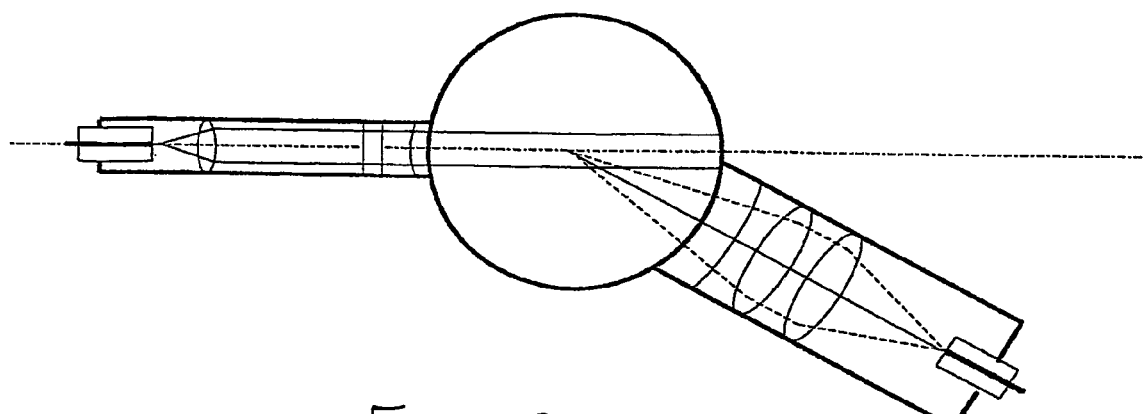
FIGS. 2a and 2b are cross-sectional views, respectively along and perpendicular to the pipe axis, of an optical system used in the prior art showing the collection optical system axis intersecting the delivery optical system axis at an angle.
Figure 2B:
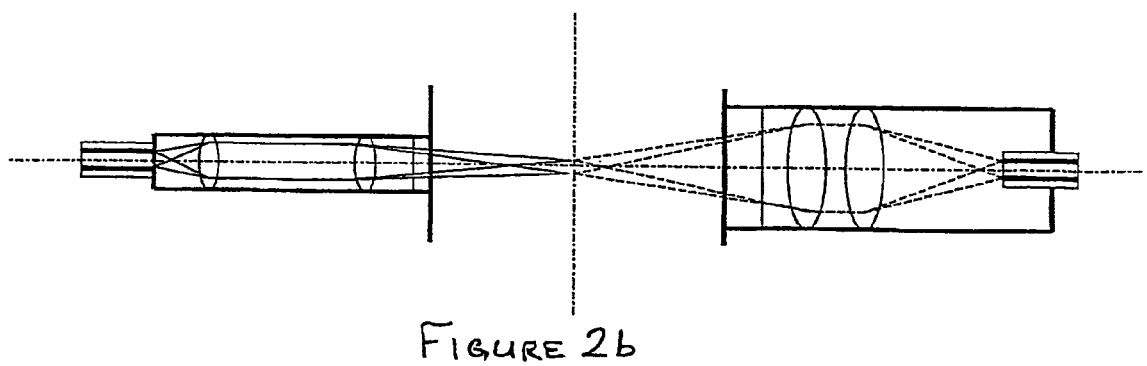
Figure 3:
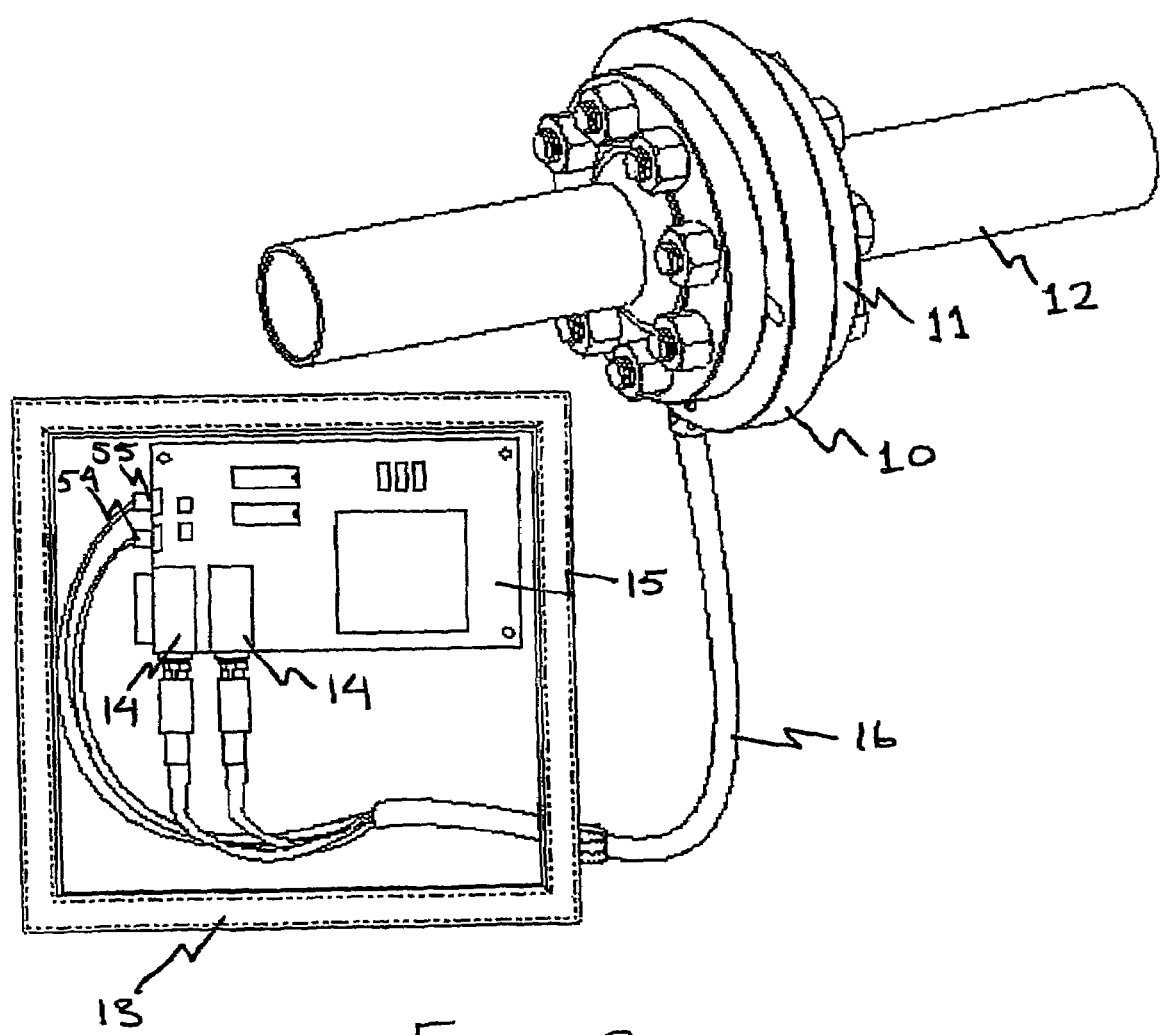
FIG. 3 is a system diagram showing the a preferred embodiment of the present invention with separate opto-mechanical head, electro-optical assembly connected by an fiber-optic extension cable.

There is shown in FIG. 3 an optical flow meter constructed in accordance with the preferred embodiment to determine the flow rate of a fluid in a pipe, by measuring the velocity of small particles carried by the fluid stream. The flow meter apparatus is comprised of an opto-mechanical head 10 inserted between adjacent flanges 11 in the pipe 12, an electro-optical assembly 13 which contains two laser light sources 14, two scatter signal photo-detectors 54 and 55, and processing electronics 15, and a fiber-optic extension cable conduit 16 which connects the electro-optical assembly 13 to the opto-mechanical head 10. In this configuration, the electro-optical assembly 13 can be located remotely so that no electrical potentials are present at the opto-mechanical head 10, which is desirable when the fluid passing through the pipe can be ignited by sparks or short circuits, such as natural gas. Furthermore, the fiber-optic terminations at the opto-mechanical head 10 are compact, robust, and dimensionally stable because they are removed from thermal loading from the electronics and the light sources.

Figure 4A:
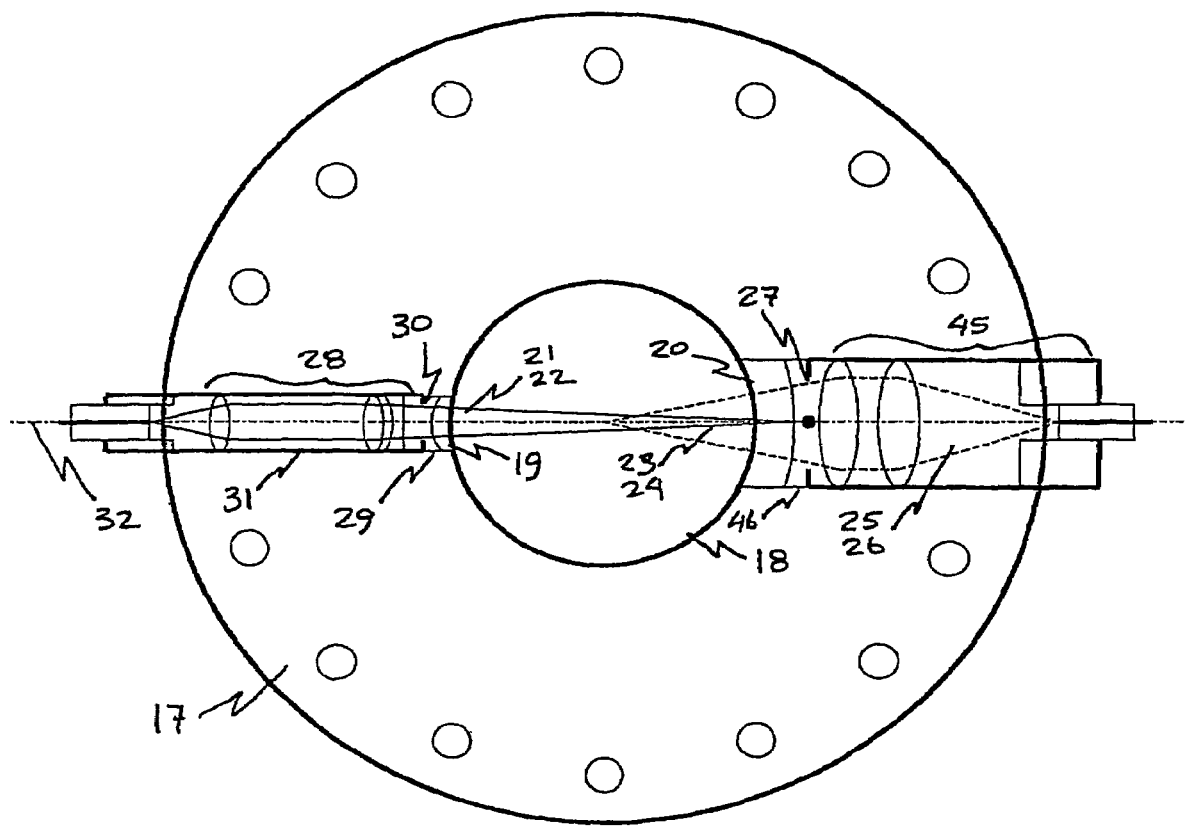
FIGS. 4a and 4b are cross-sectional views, respectively perpendicular to the pipe axis and along the optical axis, of the opto-mechanical head assembly portion of the present invention.
Figure 4B:
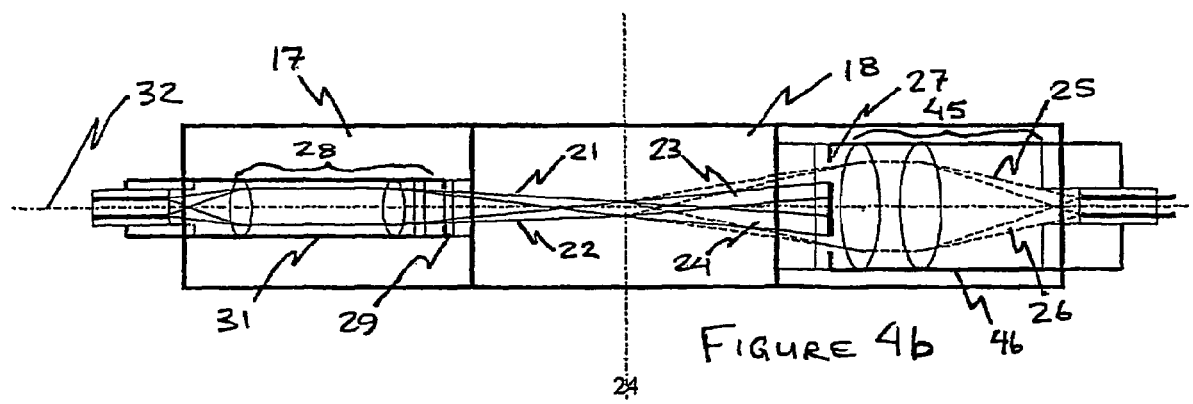

The opto-mechanical head 10 of the preferred embodiment, shown in further detail in FIG. 4, is comprised of a rigid plate housing 17 that can be clamped between flanges in the pipeline, with a central bore 18 having a diameter approximately matched with the inner pipe diameter and thus forming a contiguous sealed passageway for fluid to flow through without disruption. The central bore 18 contains two windows 19 and 20: the delivery window 19 allows delivery light beams 21 and 22 to enter the central bore 18; and the collection window 20 on the opposite side of the central bore 18, allows both unscattered light beams 23 and 24, and scattered light beams 25 and 26 to pass into the collection aperture 27. In the preferred embodiment, both windows 19 and 20 are shaped to match the cylindrical curvature of the central bore 18 to form a smooth continuous surface to minimize disruption of the fluid flow and reduce the build up of contaminants, which may be present in the fluid stream. In a further embodiment of the invention, a length of optically transparent tubing with an inner diameter approximately matched to the inner diameter of the pipe wall, may be inserted into the central bore 18 of the housing plate 17 to seal the fluid flow and allow light to pass into and out of the pipe flow.

The delivery lens system 28 is contained in a delivery lens bore 29 in the opto-mechanical plate housing 17, extending radially from the delivery window aperture 30 to the outer perimeter. The delivery lens system 28 is typically housed in a tubular mechanical housing 31 and collectively they establish an optical axis 32 for the system. The delivery lens system 28 is shown in FIGS. 5a and 5b, exaggerated in size relative to the pipe cross-section for greater clarity. Two delivery optical fibers 33 and 34 are terminated in a double bore ferrule 35, and spaced equally from and on opposite sides of the optical axis 32. The ferrule 35 is rotated around the optical axis 32 so that the tips of both fibers 33 and 34 are aligned with the pipe axis 36. The delivery light beams 21 and 22 diverge from the delivery optical fibers 33 and 34 and are approximately parallel with the optical axis 32. The delivery light beams 21 and 22 are collimated by the fiber coupling lens 37, and then focused by the delivery objective lens 38 through the delivery window 19, to form two primary focal points 39 and 40 inside the central bore 18, separated along the pipe axis 36. The separation distance between primary focal points 39 and 40 is determined by selecting the focal lengths of the delivery coupling lens 37 and objective lens 38, according to the following formula:

$$D = d_d * f_{do} / f_{dc}$$

Where D is the axial separation between focal spots in the pipe; $d_d$ is the axial separation between optical fibers 33 and 34; $f_{do}$ is the focal length of the delivery objective lens 38; and $f_{dc}$ is the focal length of the delivery coupling lens 37.

In the preferred embodiment, the optical path separation between the delivery coupling lens 37 and the objective lens 38 is selected to be equal to the sum of their focal lengths. This forms what is referred to in the art as a telecentric optical system, which means the chief ray at the focal plane remains parallel to the optical axis. The delivery light beams 21 and 22 are projected along axes parallel with the optical system axis 32, and perpendicular to the pipe axis 36 as well as the surface of the delivery window 19, as shown in FIG. 5a. This is important in applications where the refractive index of a compressable gas, such as natural gas, varies depending on the internal pressure. In the case of a non-telecentric system, the separation between focal spots would change due to the parallax caused by the refractive index change of the compressable fluid, resulting in a velocity measurement error.

Referring to FIG. 5a, a cylindrical lens 41 is disposed within the optical delivery system 28 to shift the beam focus away from the primary focal points 39 and 40 to form two secondary line foci 42 and 43 along the optical system axis 32. This has the effect of broadening the width of the beam at the primary focal spots 39 and 40 into two sheets of light, and thus increasing the cross-sectional area that intercepts the fluid flow at the velocity measurement zone. In the preferred embodiment, the focal length of the cylindrical lens 41 is chosen so that the two beams form two collinear line foci 42 and 43 at a common point on the optical system axis 32, located at or behind the surface of the collection window 20.

At the secondary foci 42 and 43, the cross-sectional area of the incident unscattered delivery beams 23 and 24 are a minimum. An optically opaque obscuration 44, approximating a thin rectangular shape, sized to be slightly larger than the unscattered beam profile at the secondary focal plane, is positioned to intercept most or all of the unscattered delivery beams 23 and 24. This allows for a maximum amount of scattered light to enter the unobscured collection aperture 27 to optimize the optical signal detection sensitivity. More specifically, the minimum extent of the beam profile subtended by the narrow dimension of the rectangular opaque obscuration 44 allows for the smallest possible angles of scattered light 25 and 26 to enter the collection aperture 27, without bias from the unscattered beams 23 and 24.

Referring back to FIG. 4, the collection lens system 45 of the preferred embodiment is contained in a collection lens bore 46 opposite to and approximately collinear with the delivery lens bore 29, extending radially from the collection window aperture 27 to the outer perimeter of the opto-mechanical plate housing 17. Referring to FIGS. 6a and 6b the collection lens system 45, shown exaggerated in size relative to the pipe cross-section for greater clarity, is comprised of an objective lens 47 and a fiber collection coupling lens 48. Scattered light beams 25 and 26, entering the collection aperture 27, are focused into two corresponding scatter collection optical fibers 49 and 50, positioned at the focal point and corresponding to each of the primary focal spots 39 and 40 in the central bore 18. The core diameters of the scatter collection fibers 49 and 50 are sized to accept a substantial portion of the scattered light beams 25 and 26, generated from points across the width of the light sheet at the velocity measurement zone, as determined by the following formula:

$$W = w_c * f_{co}/f_{cc}$$

Where W is the width of the acceptance scatter field at the primary focus points 39 and 40; $w_c$ is the diameter of the core of the scatter collection optical fibers 49 and 50; $f_{co}$ is the focal length of the collection objective lens 47; and $f_{cc}$ is the focal length of the collection coupling lens 48.

Figure 7:
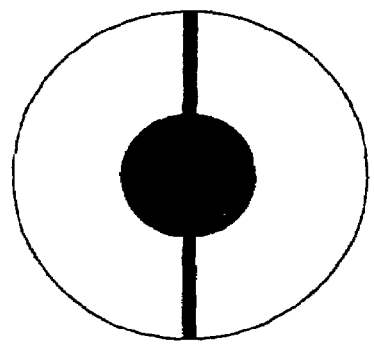
FIG. 7 is an illustration of the shape of the opaque obscuration that may be used with the preferred embodiment of the present invention, comprised of a union between a thin rectangular strip and a circular central spot.

The depth of focus of the optical system, which determines the length of the velocity measurement zone along the optical system axis 32, is affected by both the length of the beam waist of the delivery light beams 21 and 22 and the depth of focus of the collection lens system 45. Both parameters can be adjusted by selection of lenses, in accordance with the constraints provided above, but there are limits imposed by the physical size of components and housing dimensions. The depth of focus provided by the optical system is also affected by the size and shape of the opaque obscuration 44. In some cases it is desirable to reduce the depth of focus of the collection lens system 45 to further restrict the extent of the scatter measurement zone, along the optical axis 32. This can be achieved by increasing the size of the opaque obstruction 44 at the center of the optical axis 32, resulting in a shape comprised of both a rectangular strip portion overlapped with a circular central spot, as shown in FIG. 7.

Figure 8A:
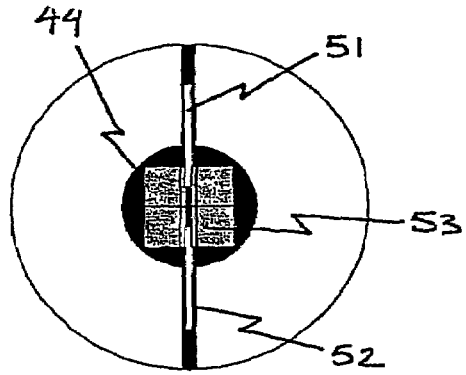
FIGS. 8a and 8b are two views of the optical reference collection assembly, comprised of a central reflector and two reference collection fibers, disposed in front of the opaque obscuration of a preferred embodiment of the present invention.
Figure 8B:
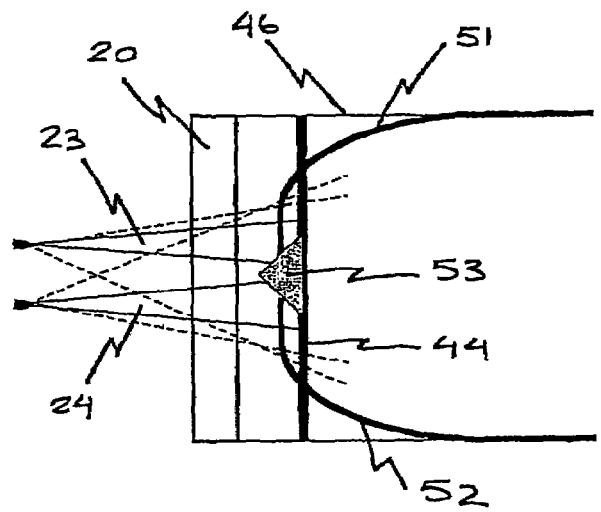

In a further preferred embodiment, a second pair of reference collection fibers 51 and 52 is positioned directly in front of the opaque obscuration 44 and means are provided to couple light from the unscattered light beams 23 and 24, as shown in FIGS. 8a and 8b. A central reflector 53 is positioned at the center of the obscuration 44 which directs a portion of each incident unscattered light beam 23 or 24 into a corresponding reference fiber 51 or 52, which are in turn routed behind the long dimension of the rectangular strip shaped opaque obscuration 44 and out the perimeter opening of the collection lens bore 46. The signal level generated by the unscattered light beams 23 and 24 coupled into the reference fibers 51 and 52 can be used to monitor the overall strength of the incident light, which may degrade over time because of a build up of contaminants fouling the optical windows 19 (not shown) and 20, or due to variations in the light source intensity.

Figure 9:
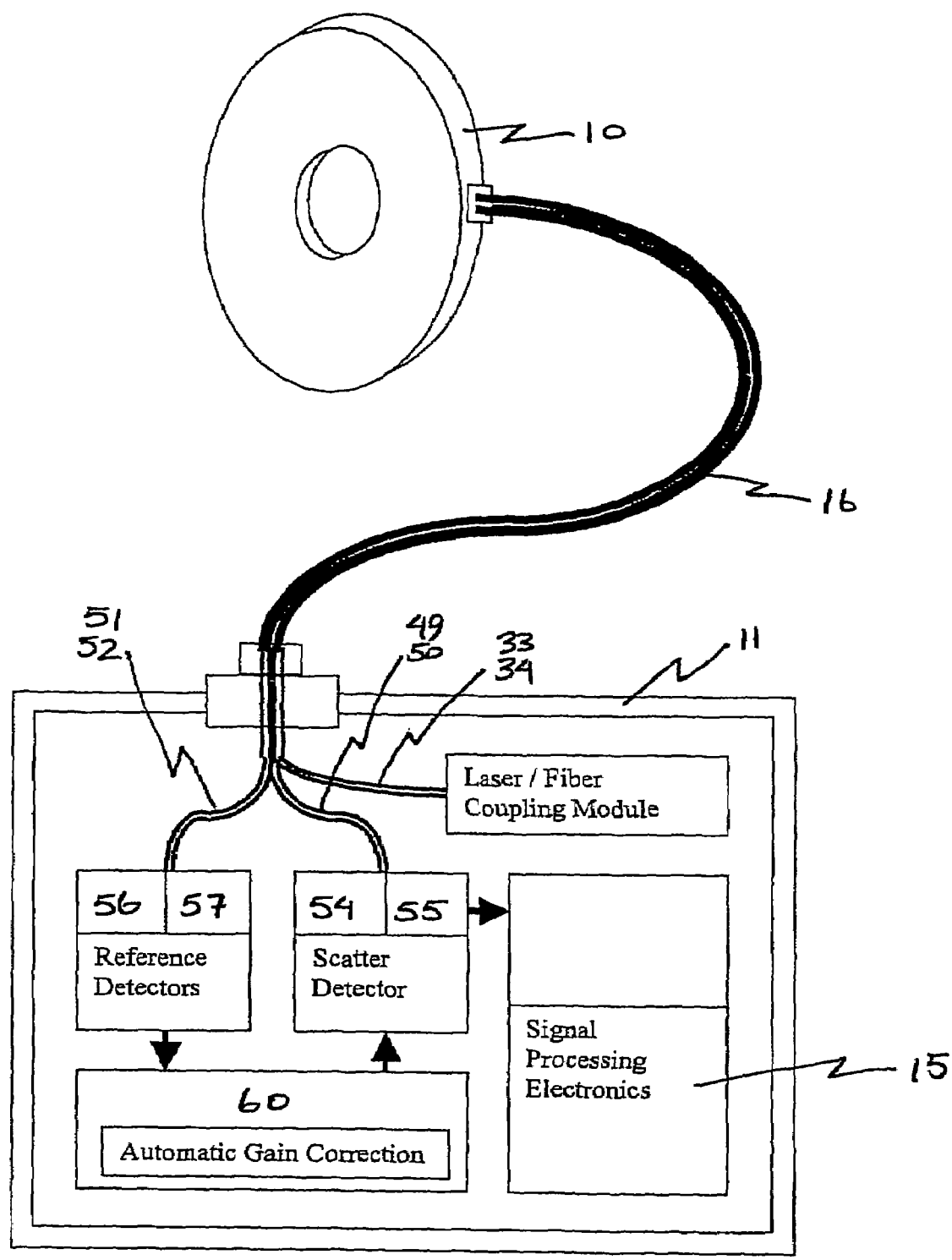
FIG. 9 is a system diagram of the present invention, comprised of separate opto-mechanical head, electro-optical assembly and extension cable, showing a block diagram of the electronics processing circuits and the flow of signals used to compensate for optical system efficiency losses.

Referring to FIG. 9, the scatter collection fibers 49 and 50, and reference collection fibers 51 and 52, are gathered with the delivery fibers 33 and 34, and sheathed in a common extension cable conduit 16 connected to the opto-electronic assembly 11, which may be located at some distance from the opto-mechanical head 10. The collection fibers 49 and 50, and 51 and 52 are coupled to corresponding scatter signal photodetectors 54 and 55 and reference signal photodetectors 56 and 57. The light coupled into the scatter collection fibers 49 and 50, and transmitted to the scatter signal detectors 54 and 55, generates electrical pulses when particles pass through the velocity measurement zone, and processing electronics 15 are provided to determine the time of flight delay by correlating the electrical signals from the two scatter detectors 54 and 55. The reference signals generated by the reference detectors 56 an 57 may be used to adjust the gain of the scatter detector circuit 60, to compensate for optical signal loss due to fouling of the optical windows 19 and 20.

In an alternative embodiment of the invention, shown in FIGS. 10a and 10b, the telecentric delivery lens system 28 provides a delivery coupling lens 61 (may be a compound lens) and a modified ferrule 62 with two facets 63 and 64, polished on the face of the ferrule 62 and tilted equally away from the optical system axis 32. The resulting delivery light beams 21 and 22 are refracted at an angle as they exit the delivery optical fibers 33 and 34, and cross over the optical axis 32 at a distance in front of the delivery coupling lens 61 equal to its focal length, thus generating the same telecentric alignment with a more compact optical configuration.

Referring also to FIGS. 10a and 10b, a cylindrical delivery coupling lens 65 may also be added to the delivery lens system 28 disposed after the fiber ferrule 62 to collimate the delivery light beams 21 and 22 in the transverse axis. This allows for independent control of the width of the light sheet at the primary focus spots 39 and 40 by selecting the focal length of the cylindrical delivery lens 65. The focal length of the cylindrical objective lens 41 must also be shortened (negative lens) to compensate for the focal shift introduced by the cylindrical delivery lens 65, so that the secondary foci 42 and 43 remain coincident with the opaque obscuration plane 44.

Figure 11A:
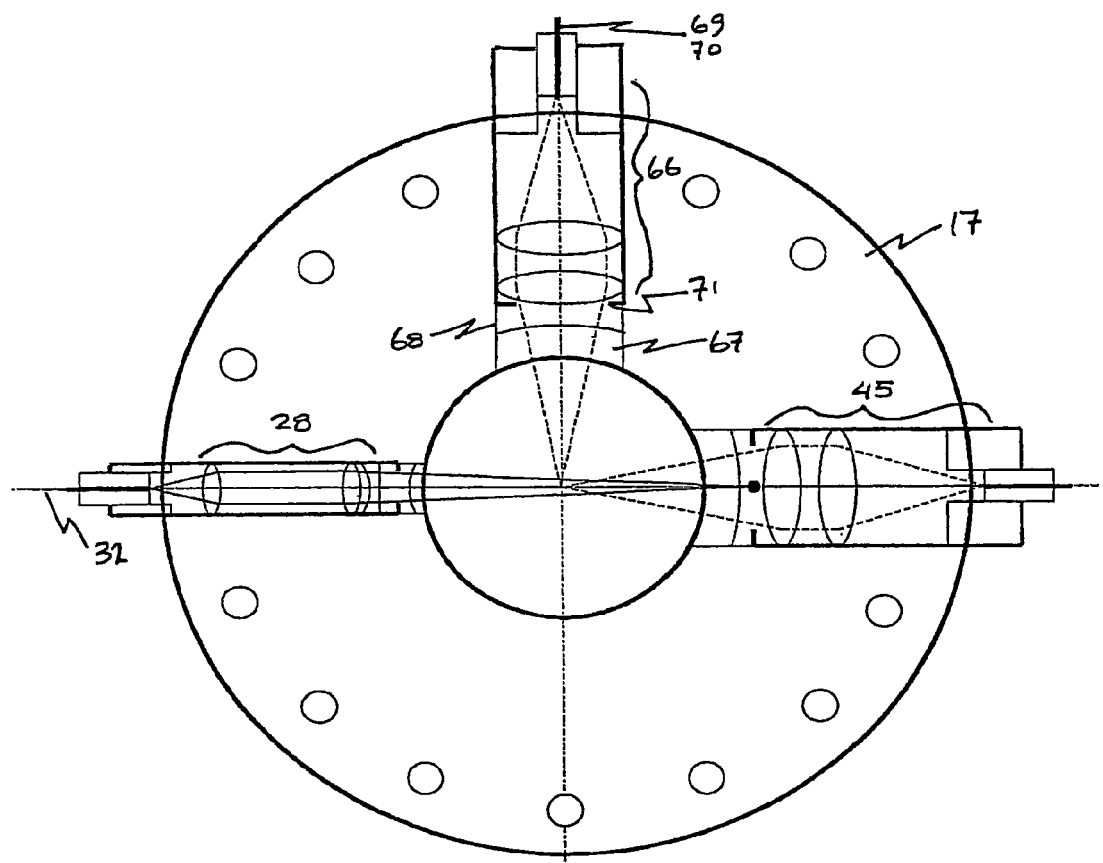
FIGS. 11a and 11b are cross-section views, respectively perpendicular to the pipe axis and along the optical system axis, showing an alternate embodiment of the present invention, providing a second collection optical system to detect light scattered at large angles, such that the amplitude of the detected light signal is used to determine the size of the scattering particle.
Figure 11B:
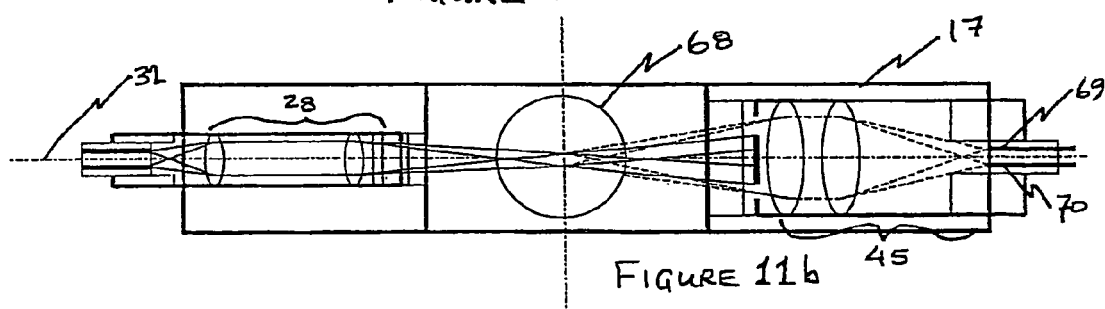

In another embodiment of the invention, shown in FIG. 11, a secondary collection lens system 66 is disposed behind a third optical window 67 in a third bore 68 in the optomechanical plate housing 17, shown at an angle perpendicular to the optical system axis 32 of the delivery and primary collection lens systems 28 and 45. The secondary collection lens system 66 does not incorporate any obscurations or reference fibers, but otherwise may be identical to the primary collection lens system 45. A secondary pair of collection fibers 69 and 70 is disposed to accept the scattered light coupled into the secondary collection aperture 71, connected to a second pair of measuring photodetectors (not shown). The amount of light scattered at large angles, away from the optical system axis 32 is strongly dependent on the size of the scattering particles, so by measuring the ratio of light signal intensities, information about the size of the scattering particles carried by the fluid stream can be determined.

Figure 12:
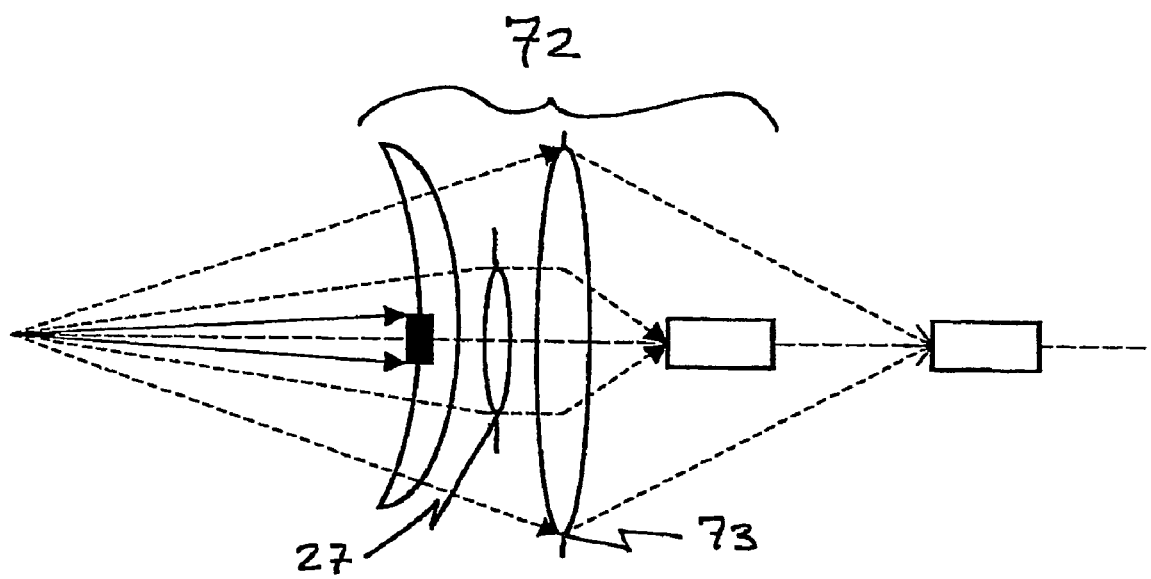
FIG. 12, showing an alternative embodiment of the optical collection system shown in FIG. 12, where the second collection optical system is collinear with the first collection optical system axis.

Yet another embodiment of the invention, shown in FIG. 12, provides a second collection lens system 72 with an aperture 73 larger than the aperture of the first collecting system 27, and both systems are disposed collinearly. The second collection lens system 72 collects the light that is scattered at larger angles within a solid angle defined by the difference between the apertures 73 and 27 of both systems. The comparison of the amount of light collected by each system gives the information about the size and shape of the particles.

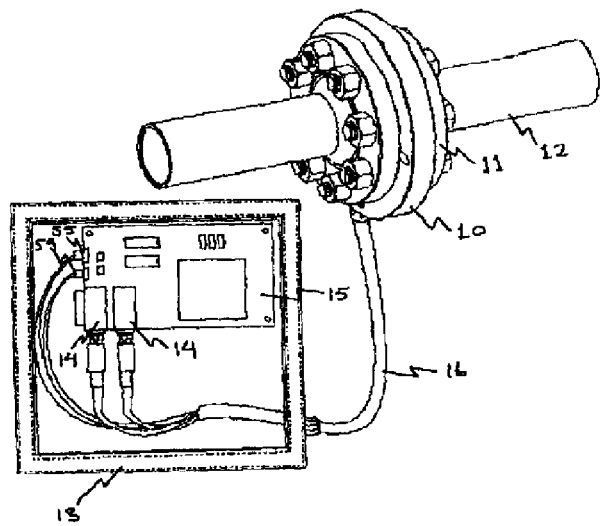

What is claimed is:

1. An apparatus for measuring the velocity of particles carried by a fluid, flowing through a pipe, comprising:
   (a) at least one light source and means for generating two separate beams of light;
   (b) a first transparent optical window in the pipe wall that contains the fluid flow within the pipe and allows the beams of light to enter the inside pipe volume;
   (c) an optical delivery system, having an optical axis, which directs said two beams of light through said first optical window, so that the beams form two focal spots inside the pipe, aligned approximately at the same position within the pipe cross-section but at different points along the pipe axis with a known separation between them;
   (d) a second transparent optical window in the pipe wall, disposed approximately on the opposite side of the pipe wall to the first optical window, that contains the fluid flow within the pipe and allows light to exit the inside pipe volume;
   (e) at least one measuring light detector means for detecting light scattered by particles carried by the fluid, and converting the time varying detected light amplitude to a corresponding measuring electronic signal;
   (f) an optical collection system, having an optical axis that is approximately collinear with the optical axis of said optical delivery system, that collects light scattered by particles carried in the fluid flow within a first solid angle subtended from said focal spots, and focuses said scattered light on to said measuring light detector means;
   (g) an opaque obscuration to absorb unscattered light, disposed approximately on the optical axis after said focal spots, said obscuration subtending a second solid angle from said focal spots, which is smaller than said first solid angle so that said scattered light that passes through the unobscured portion of said first solid angle, reaches the measuring light detector means; and
   (h) an electronic processing means that receives said measuring electronic signals detected by the light detector means, wherein said measuring electronic signals are processed to determine the time of flight delay of particles passing through the two focal spots, and further means for calculating the particle velocity or fluid flow rate.

2. The device according to claim 1, wherein the light source is comprised of one or more lasers.

3. The device according to claim 1, wherein the means for generating said two beams of light includes coupling the light source into at least one optical fiber.

4. The device according to claim 1, wherein the light detector means is comprised of an optical fiber coupled to a photo-detector.

5. The device according to claim 1, wherein the light detector means includes a first and second light detector field, aligned so that light scattered from the first focal spot is coupled to the first light detector field, and light scattered from the second focal spot is coupled to the second light detector field.

6. The device according to claim 5, wherein the light detector means includes a first and second collection optical fiber coupled to corresponding first and second light detector means.

7. A device according to claim 1, wherein the optical axes of said optical delivery system and said optical collection system are approximately perpendicular to the flow direction.

8. A device according to claim 1, wherein the chief ray of each of said two beams of light is approximately perpendicular to the axis of said pipe, so that the chief rays do not deviate if the refractive index of the fluid changes.

9. A device according to claim 1, wherein a mechanical housing with a central hole approximately matched in size and shape to the cross-section of the pipe, is inserted into the pipeline and mated to fore and aft pipe sections so as to form a continuous and sealed passage for fluid to flow through, said mechanical housing incorporating said first and second windows, said optical delivery system and said optical collection system.

10. A device according to claim 1, wherein the first and second window have substantially cylindrical inner surfaces, approximately matched to the surface of the inner pipe wall.

11. A device according to claim 1, wherein the first and second window are replaced by a length of transparent tubing, with an inner diameter matched to the inner diameter of the pipe to contain the fluid inside the pipe and allow light to pass in from the optical delivery system and through to the optical collection system.

12. A device according to claim 1, wherein the optical delivery system includes cylindrical optical lens means to expand the width of the focal spots in the plane of the pipe cross-section.

13. A device according to claim 12, wherein the cylindrical lens means generates a second focal point approximately at said opaque obscuration plane, such that the beams form a pair of focal line segments with an axis parallel with the pipe flow and passing through the center of the optical system axis.

14. A device according to claim 1, wherein means are provided to intercept a portion of the unscattered light, in front of the opaque obstruction but behind the second optical window, and coupling the intercepted light on to at least one reference detector means, and using the detected signal level to adjust the gain of the photodetectors to compensate for variations in the incident light intensity.

15. A device according to claim 1, wherein a second optical collection system is provided, with a second collection axis, in the same plane as the delivery optical axis and the first collection axis, and intersecting the focal spots, wherein light scattered by particles in the fluid stream are coupled into a second light detector means, for the purpose of analyzing the size and/or shape of particles traveling in the fluid stream by comparing the ratio of the amplitudes of the first detected light signals with the second detected light signals.

16. A device according to claim 15, wherein said axis of said second optical collection system is approximately collinear with said first optical collection axis, and wherein said second optical collection system has a larger optical aperture than said first optical collection system, that allows scattered light to be collected at higher scattered angles.

* * * * *

UNITED STATES PATENT AND TRADEMARK OFFICE
CERTIFICATE OF CORRECTION

| | | |
|---|---|---|
| PATENT NO. | : 7,265,832 B2 | Page 1 of 5 |
| APPLICATION NO. | : 10/570323 | |
| DATED | : September 4, 2007 | |
| INVENTOR(S) | : Derek Montgomery, Daryl James and David Yue Yan | |

It is certified that error appears in the above-identified patent and that said Letters Patent is hereby corrected as shown below:

Col. 9, lines 35-67 - Col. 10, lines 1-5
Claims 1-16 are replaced with claims 1-29 as follows:

1. An apparatus for measuring the velocity of particles carried by a fluid, flowing through a pipe, comprising:

(a) at least one light source coupled to two optical fibers for generating two separate beams of light;

(b) a first means in the pipe wall for containing the fluid flow within the pipe and allowing the beams of light to enter the inside pipe volume;

(c) a telecentric optical delivery system having a single aperture and a single optical axis, which directs said two beams of light through said first means in the pipe wall, so that the beams form two focal spots inside the pipe, aligned at the same position within the pipe cross-section but at different points along the pipe axis with a known separation between them;

(d) a second means in the pipe wall, disposed on the opposite side of the pipe wall to the first means in the pipe wall, for containing the fluid flow within the pipe and allowing light to exit the inside pipe volume;

(e) at least one measuring light detector means for detecting light scattered by the particles carried by the fluid, and converting the time varying detected light amplitude to a corresponding measuring electronic signal;

(f) an optical collection system, having an optical axis that is substantially collinear with the optical axis of said optical delivery system, that collects light scattered by particles carried in the fluid flow within a first solid angle subtended from said focal spots, and focuses said scattered light on to said measuring light detector means;

Signed and Sealed this
First Day of March, 2011

David J. Kappos
*Director of the United States Patent and Trademark Office*

(g) an opaque obscuration to absorb unscattered light, disposed on the optical axis after said focal spots, said obscuration subtending a second solid angle from said focal spots, which is smaller than said first solid angle so that said scattered light that passes through the unobscured portion of said first solid angle, reaches the measuring light detector means; and Col. 10, lines 6-34 should read, (h) an electronic processing means that receives said measuring electronic signals detected by the light detector means, wherein said measuring electronic signals are processed to determine the time of flight delay of particles passing through the two focal spots, and further means for calculating the particle velocity or fluid flow rate.

2. A device according to claim 1, wherein the telecentric optical delivery system comprises a focussing lens having a focal length and wherein the two optical fibers have two facets at the ends thereof, the two facets being tilted equally away from the optical axis of the delivery system for refracting said beams of light toward the optical axis of the delivery system to intersect the optical axis in front of the focussing lens at a distance equal to the focal length of the focussing lens.

3. A device according to claim 1, wherein the light source is comprised of one or more lasers.

4. A device according to claim 1, wherein the light detector means is comprised of an optical fiber coupled to a photo-detector.

5. A device according to claim 1, wherein the light detector means includes a first and second light detector field, aligned so that light scattered from a first of said two focal spots is coupled to the first light detector field, and light scattered from a second of said two focal spots is coupled to the second light detector field.

6. A device according to claim 5, wherein the light detector means comprises a first collection optical fiber coupled to a first light detector means and a second collection optical fiber coupled to a second light detector means.

7. A device according to claim 1, wherein the optical axis of said optical delivery system and said optical collection system are substantially perpendicular to the flow direction.

Col. 10, lines 35-65 should read,

8. A device according to claim 1, wherein a chief ray of each of said two beams of light is substantially perpendicular to the axis of said pipe, so that the chief rays do not deviate if the refractive index of the fluid changes.

9. A device according to claim 1, wherein a mechanical housing with a central hole substantially matched in size and shape to the cross-section of the pipe, is inserted into the pipeline and mated to fore and aft pipe sections so as to form a continuous and sealed passage for fluid to flow through, said mechanical housing incorporating said first and second means in the pipe wall, said optical delivery system and said optical collection system.

10. A device according to claim 1, wherein the first and second means in the pipe wall comprise first and second transparent optical windows having substantially cylindrical inner surfaces, substantially matched to the surface of the inner pipe wall.

11. A device according to claim 1, wherein the first and second means in the pipe wall comprise a length of transparent tubing, with an inner diameter matched to the inner diameter of the pipe to contain the fluid inside the pipe and allow light to pass in from the optical delivery system and through to the optical collection system.

12. A device according to claim 1, wherein the optical delivery system includes cylindrical optical lens means to expand the width of the focal spots in the plane of the pipe cross-section.

13. A device according to claim 12, wherein the cylindrical lens means generates secondary foci at a plane of said opaque obscuration, such that the beams form a pair of collinear focal line segments parallel to the pipe axis and passing through the center of the optical system axis.

Col. 10, lines 66-67 - Col. 11, lines 1-5 should read,

14. A device according to claim 1, wherein means are provided to intercept a portion of the unscattered light, in front of the opaque obstruction but behind the second optical window, and coupling the intercepted light on to at least one reference detector means, and using the detected signal level from the intercepted light to adjust the gain of the measuring light detector means to compensate for variations in the incident light intensity.

Col. 11, lines 6-12 and Col. 12, lines 1-3,

15. A device according to claim 1, wherein a second optical collection system is provided, with a second collection axis, in the same plane as the delivery optical axis and the first collection axis, and intersecting the focal spots, wherein light scattered by particles in the fluid stream are coupled into a second light detector means to produce second detected light signals, for the purpose of analyzing the at least one of the size and shape of particles travelling in the fluid stream by comparing the ratio of the amplitudes of the first detected light signals with the second detected light signals.

Col. 12, lines 4-10 should read,

16. A device according to claim 15, wherein said axis of said second optical collection system is substantially collinear with said first optical collection axis, and wherein said second optical collection system has a larger optical aperture than said first optical collection system, that allows scattered light to be collected at higher scattered angles.

CERTIFICATE OF CORRECTION (continued)
U.S. Pat. No. 7,265,832 B2

Col. 12, lines 11-14 should read,

17. A device according to claim 1, wherein the telecentric optical delivery system includes cylindrical optical lens means for expanding the width of the focal spots in the plane of the pipe cross-section and for generating secondary foci at a plane of said opaque obscuration, such that the beams form a pair of collinear focal line segments parallel to the pipe axis and passing through the center of the optical system axis.

Col. 12, line 15 should read,

18. A device according to claim 17, wherein the light source is comprised of one or more lasers.

Col. 13, lines 1-2 should read,

19. A device according to claim 17, wherein the light detector means is comprised of an optical fiber coupled to a photo-detector.

Col. 13, lines 3-5 should read,

20. A device according to claim 17, wherein the light detector means includes a first and second light detector field, aligned so that light scattered from a first of said two focal spots is coupled to the first light detector field, and light scattered from a second of said two focal spots is coupled to the second light detector field.

Col. 13, lines 6-8 should read,

21. A device according to claim 20, wherein the light detector means comprises a first collection optical fiber coupled to a first light detector means and a second collection optical fiber coupled to a second light detector means.

Col. 13, lines 9-10 should read,

22. A device according to claim 17, wherein the optical axis of said optical delivery system and said optical collection system are substantially perpendicular to the flow direction.

Col. 13, lines 11-13 should read,

23. A device according to claim 17, wherein a chief ray of each of said two beams of light is substantially perpendicular to the axis of said pipe, so that the chief rays do not deviate if the refractive index of the fluid changes.

CERTIFICATE OF CORRECTION (continued)
U.S. Pat. No. 7,265,832 B2

Col. 13, lines 14-19 should read,

24. A device according to claim 17, wherein a mechanical housing with a central hole substantially matched in size and shape to the cross-section of the pipe, is inserted into the pipeline and mated to fore and aft pipe sections so as to form a continuous and sealed passage for fluid to flow through, said mechanical housing incorporating said first and second means in the pipe wall, said optical delivery system and said optical collection system.

Col. 13, lines 20-22 should read,

25. A device according to claim 17, wherein the first and second means in the pipe wall comprise first and second transparent optical windows having substantially cylindrical inner surfaces, substantially matched to the surface of the inner pipe wall.

Col. 13, lines 23-25 should read,

26. A device according to claim 17, wherein the first and second means in the pipe wall comprise a length of transparent tubing, with an inner diameter matched to the inner diameter of the pipe to contain the fluid inside the pipe and allow light to pass in from the optical delivery system and through to the optical collection system.

Col. 13, lines 26-30 should read,

27. A device according to claim 17, wherein means are provided to intercept a portion of the unscattered light, in front of the opaque obstruction but behind the second optical window, and coupling the intercepted light on to at least one reference detector means, and using the detected signal level from the intercepted light to adjust the gain of the measuring light detector means to compensate for variations in the incident light intensity.

Col. 13, lines 31-36 should read,

28. A device according to claim 17, wherein a second optical collection system is provided, with a second collection axis, in the same plane as the delivery optical axis and the first collection axis, and intersecting the focal spots, wherein light scattered by particles in the fluid stream are coupled into a second light detector means to produce second detected light signals, for the purpose of analyzing the at least one of the size and shape of particles travelling in the fluid stream by comparing the ratio of the amplitudes of the first detected light signals with the second detected light signals.

Col. 13, lines 37-40 should read,

29. A device according to claim 28, wherein said axis of said second optical collection system is substantially collinear with said first optical collection axis, and wherein said second optical collection system has a larger optical aperture than said first optical collection system, that allows scattered light to be collected at higher scattered angles.

UNITED STATES PATENT AND TRADEMARK OFFICE
CERTIFICATE OF CORRECTION

Page 1 of 6

| | |
|---|---|
| PATENT NO. | : 7,265,832 B2 |
| APPLICATION NO. | : 10/570323 |
| DATED | : September 4, 2007 |
| INVENTOR(S) | : Derek Montgomery, Daryl James and David Yue Yan |

It is certified that error appears in the above-identified patent and that said Letters Patent is hereby corrected as shown below:

Delete the title page of patent and substitute therefore the attached title page showing the corrected number of claims in patent.

Col. 9, line 36 - Col. 12, line 9
Delete Claims 1-16 and replace with claims 1-29 as follows:

1. An apparatus for measuring the velocity of particles carried by a fluid, flowing through a pipe, comprising:

(a) at least one light source coupled to two optical fibers for generating two separate beams of light;

(b) a first means in the pipe wall for containing the fluid flow within the pipe and allowing the beams of light to enter the inside pipe volume;

(c) a telecentric optical delivery system having a single aperture and a single optical axis, which directs said two beams of light through said first means in the pipe wall, so that the beams form two focal spots inside the pipe, aligned at the same position within the pipe cross-section but at different points along the pipe axis with a known separation between them;

(d) a second means in the pipe wall, disposed on the opposite side of the pipe wall to the first means in the pipe wall, for containing the fluid flow within the pipe and allowing light to exit the inside pipe volume;

(e) at least one measuring light detector means for detecting light scattered by the particles carried by the fluid, and converting the time varying detected light amplitude to a corresponding measuring electronic signal;

Signed and Sealed this
Fifth Day of April, 2011

David J. Kappos
*Director of the United States Patent and Trademark Office*

(f) an optical collection system, having an optical axis that is substantially collinear with the optical axis of said optical delivery system, that collects light scattered by particles carried in the fluid flow within a first solid angle subtended from said focal spots, and focuses said scattered light on to said measuring light detector means;

(g) an opaque obscuration to absorb unscattered light, disposed on the optical axis after said focal spots, said obscuration subtending a second solid angle from said focal spots, which is smaller than said first solid angle so that said scattered light that passes through the unobscured portion of said first solid angle, reaches the measuring light detector means; and (h) an electronic processing means that receives said measuring electronic signals detected by the light detector means, wherein said measuring electronic signals are processed to determine the time of flight delay of particles passing through the two focal spots, and further means for calculating the particle velocity or fluid flow rate.

2. A device according to claim 1, wherein the telecentric optical delivery system comprises a focusing lens having a focal length and wherein the two optical fibers have two facets at the ends thereof, the two facets being tilted equally away from the optical axis of the delivery system for refracting said beams of light toward the optical axis of the delivery system to intersect the optical axis in front of the focusing lens at a distance equal to the focal length of the focusing lens.

3. A device according to claim 1, wherein the light source is comprised of one or more lasers.

4. A device according to claim 1, wherein the light detector means is comprised of an optical fiber coupled to a photo-detector.

5. A device according to claim 1, wherein the light detector means includes a first and second light detector field, aligned so that light scattered from a first of said two focal spots is coupled to the first light detector field, and light scattered from a second of said two focal spots is coupled to the second light detector field.

6. A device according to claim 5, wherein the light detector means comprises a first collection optical fiber coupled to a first light detector means and a second collection optical fiber coupled to a second light detector means.

7. A device according to claim 1, wherein the optical axis of said optical delivery system and said optical collection system are substantially perpendicular to the flow direction.

8. A device according to claim 1, wherein a chief ray of each of said two beams of light is substantially perpendicular to the axis of said pipe, so that the chief rays do not deviate if the refractive index of the fluid changes.

9. A device according to claim 1, wherein a mechanical housing with a central hole substantially matched in size and shape to the cross-section of the pipe, is inserted into the pipeline and mated to fore and aft pipe sections so as to form a continuous and sealed passage for fluid to flow through, said mechanical housing incorporating said first and second means in the pipe wall, said optical delivery system and said optical collection system.

10. A device according to claim 1, wherein the first and second means in the pipe wall comprise first and second transparent optical windows having substantially cylindrical inner surfaces, substantially matched to the surface of the inner pipe wall.

11. A device according to claim 1, wherein the first and second means in the pipe wall comprise a length of transparent tubing, with an inner diameter matched to the inner diameter of the pipe to contain the fluid inside the pipe and allow light to pass in from the optical delivery system and through to the optical collection system.

12. A device according to claim 1, wherein the optical delivery system includes cylindrical optical lens means to expand the width of the focal spots in the plane of the pipe cross-section.

13. A device according to claim 12, wherein the cylindrical lens means generates secondary foci at a plane of said opaque obscuration, such that the beams form a pair of collinear focal line segments parallel to the pipe axis and passing through the center of the optical system axis.

14. A device according to claim 1, wherein means are provided to intercept a portion of the unscattered light, in front of the opaque obstruction but behind the second optical window, and coupling the intercepted light on to at least one reference detector means, and using the detected signal level from the intercepted light to adjust the gain of the measuring light detector means to compensate for variations in the incident light intensity.

15. A device according to claim 1, wherein a second optical collection system is provided, with a second collection axis, in the same plane as the delivery optical axis and the first collection axis, and intersecting the focal spots, wherein light scattered by particles in the fluid stream are coupled into a second light detector means to produce second detected light signals, for the purpose of analyzing the at least one of the size and shape of particles travelling in the fluid stream by comparing the ratio of the amplitudes of the first detected light signals with the second detected light signals.

16. A device according to claim 15, wherein said axis of said second optical collection system is substantially collinear with said first optical collection axis, and wherein said second optical collection system has a larger optical aperture than said first optical collection system, that allows scattered light to be collected at higher scattered angles.

17. A device according to claim 1, wherein the telecentric optical delivery system includes cylindrical optical lens means for expanding the width of the focal spots in the plane of the pipe cross-section and for generating secondary foci at a plane of said opaque obscuration, such that the beams form a pair of collinear focal line segments parallel to the pipe axis and passing through the center of the optical system axis.

18. A device according to claim 17, wherein the light source is comprised of one or more lasers.

19. A device according to claim 17, wherein the light detector means is comprised of an optical fiber coupled to a photo-detector.

20. A device according to claim 17, wherein the light detector means includes a first and second light detector field, aligned so that light scattered from a first of said two focal spots is coupled to the first light detector field, and light scattered from a second of said two focal spots is coupled to the second light detector field.

21. A device according to claim 20, wherein the light detector means comprises a first collection optical fiber coupled to a first light detector means and a second collection optical fiber coupled to a second light detector means.

22. A device according to claim 17, wherein the optical axis of said optical delivery system and said optical collection system are substantially perpendicular to the flow direction.

23. A device according to claim 17, wherein a chief ray of each of said two beams of light is substantially perpendicular to the axis of said pipe, so that the chief rays do not deviate if the refractive index of the fluid changes.

24. A device according to claim 17, wherein a mechanical housing with a central hole substantially matched in size and shape to the cross-section of the pipe, is inserted into the pipeline and mated to fore and aft pipe sections so as to form a continuous and sealed passage for fluid to flow through, said mechanical housing incorporating said first and second means in the pipe wall, said optical delivery system and said optical collection system.

25. A device according to claim 17, wherein the first and second means in the pipe wall comprise first and second transparent optical windows having substantially cylindrical inner surfaces, substantially matched to the surface of the inner pipe wall.

26. A device according to claim 17, wherein the first and second means in the pipe wall comprise a length of transparent tubing, with an inner diameter matched to the inner diameter of the pipe to contain the fluid inside the pipe and allow light to pass in from the optical delivery system and through to the optical collection system.

CERTIFICATE OF CORRECTION (continued)
U.S. Pat. No. 7,265,832 B2

27. A device according to claim 17, wherein means are provided to intercept a portion of the unscattered light, in front of the opaque obstruction but behind the second optical window, and coupling the intercepted light on to at least one reference detector means, and using the detected signal level from the intercepted light to adjust the gain of the measuring light detector means to compensate for variations in the incident light intensity.

28. A device according to claim 17, wherein a second optical collection system is provided, with a second collection axis, in the same plane as the delivery optical axis and the first collection axis, and intersecting the focal spots, wherein light scattered by particles in the fluid stream are coupled into a second light detector means to produce second detected light signals, for the purpose of analyzing the at least one of the size and shape of particles travelling in the fluid stream by comparing the ratio of the amplitudes of the first detected light signals with the second detected light signals.

29. A device according to claim 28, wherein said axis of said second optical collection system is substantially collinear with said first optical collection axis, and wherein said second optical collection system has a larger optical aperture than said first optical collection system, that allows scattered light to be collected at higher scattered angles.

United States Patent
Montgomery et al.

(10) Patent No.: US 7,265,832 B2
(45) Date of Patent: Sep. 4, 2007

(54) OPTICAL FLOW METER FOR MEASURING GASES AND LIQUIDS IN PIPELINES

(75) Inventors: Derek Montgomery, New Westminster (CA); Daryl James, Burnaby (CA); David Yue Yan, Coquitlam (CA)

(73) Assignee: Photon Control Inc., Burnaby, British Columbia (*) Notice: Subject to any disclaimer, the term of this patent is extended or adjusted under 35 U.S.C. 154(b) by 0 days.

(21) Appl. No.: 10/570,323

(22) PCT Filed: Sep. 3, 2004

(86) PCT No.: PCT/CA2004/001593
§ 371 (c)(1),
(2), (4) Date: Oct. 3, 2006

(87) PCT Pub. No.: WO2005/022170
PCT Pub. Date: Mar. 10, 2005

(65) Prior Publication Data
US 2007/0064218 A1 Mar. 22, 2007

(30) Foreign Application Priority Data
Sep. 3, 2003 (CA) .................... 2439242

(51) Int. Cl.
G01P 3/36 (2006.01)
G01N 21/00 (2006.01)
G01F 1/708 (2006.01)

(52) U.S. Cl. ............... 356/338; 356/336; 356/337; 356/28; 250/574; 250/222.2; 73/861.05

(58) Field of Classification Search ........ 356/335, 343, 356/28, 28.5; 250/573–575, 214 DC, 222.2; 73/861.05
See application file for complete search history.

(56) References Cited
U.S. PATENT DOCUMENTS
3,680,961 A * 8/1972 Rudd .................... 356/335
4,201,467 A 5/1980 Hartmann et al.
(Continued)

FOREIGN PATENT DOCUMENTS
DE  4130526  3/1992

Primary Examiner—Sang H. Nguyen
(74) Attorney, Agent, or Firm—Oyen Wiggs Green & Mutala; Richard A. Johnson

(57) ABSTRACT

An optical system design for measuring the velocity of fluids flowing through pipes or other conduits is disclosed. The optical system is comprised of a means for delivering two beams through a window in the wall of the pipe, focused to two points aligned along an axis of the pipe and separated by a known distance, and means for detecting light that is scattered by particles carried in the fluid stream through a second window, that is disposed on the opposite side of the pipe. By measuring the time delay between detected signals, the velocity of the fluid can be determined. The delivered light beams are focused in a shallow cone of light and are blocked by an obstruction disposed behind the second window. The scattered light passes through an aperture behind the second window that surrounds the obscuration, and is focused on to a detector surface.

29 Claims, 11 Drawing Sheets